United States Patent
Lifshitz-Liron et al.

(10) Patent No.: US 7,294,735 B2
(45) Date of Patent: Nov. 13, 2007

(54) PURIFICATION OF CINACALCET

(75) Inventors: Revital Lifshitz-Liron, Hertzlia (IL); Yuriy Raizi, Natanya (IL); Revital Ramaty, Ramat-Hasharon (IL); Esti Marom, Ramat Gan (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/440,246

(22) Filed: May 23, 2006

(65) Prior Publication Data

US 2007/0060645 A1 Mar. 15, 2007

Related U.S. Application Data

(60) Provisional application No. 60/684,152, filed on May 23, 2005, provisional application No. 60/698,613, filed on Jul. 11, 2005, provisional application No. 60/702,918, filed on Jul. 26, 2005, provisional application No. 60/734,669, filed on Nov. 7, 2005, provisional application No. 60/738,827, filed on Nov. 21, 2005, provisional application No. 60/696,981, filed on Jul. 5, 2005, provisional application No. 60/697,111, filed on Jul. 6, 2005, provisional application No. 60/701,232, filed on Jul. 20, 2005, provisional application No. 60/706,910, filed on Aug. 9, 2005, provisional application No. 60/735,126, filed on Nov. 8, 2005, provisional application No. 60/794,804, filed on Apr. 24, 2006, provisional application No. 60/730,050, filed on Oct. 24, 2005, provisional application No. 60/732,083, filed on Oct. 31, 2005, provisional application No. 60/733,008, filed on Nov. 2, 2005, provisional application No. 60/741,787, filed on Dec. 1, 2005, provisional application No. 60/750,910, filed on Dec. 15, 2005.

(51) Int. Cl.
*C07C 229/00* (2006.01)
(52) U.S. Cl. .......................... 560/41; 560/28; 514/487
(58) Field of Classification Search .................. 560/41, 560/28; 514/487
See application file for complete search history.

(56) References Cited

U.S. PATENT DOCUMENTS

| | | | |
|---|---|---|---|
| 4,966,988 | A | 10/1990 | Schinski et al. |
| 5,648,541 | A | 7/1997 | Van Wagenen et al. |
| 6,011,068 | A | 1/2000 | Nemeth et al. |
| 6,031,003 | A | 2/2000 | Nemeth et al. |
| 6,211,244 | B1 | 4/2001 | Van Wagenen et al. |
| 6,313,146 | B1 | 11/2001 | Van Wagenen et al. |
| 2005/0147669 | A1 | 7/2005 | Lawrence et al. |

OTHER PUBLICATIONS

"Senslpar (Cinacalcet HCl) Tablets" Summary Basis of Approval of New Drug Application #21-688 By FDA, (2004).
J. Iqbal, et al. "Cinacalcet Hydrochloride" *IDrugs*, vol. 6, No. 6, p. 587-592, (2003).
L.A. Sorbera, et al. "Cinacalcet Hydrochloride" *Drugs of the Future*, vol. 27, No. 9, p. 831-836, (2002).
X. Wang, et al. "Synthesis of Cinacalcet Congeners" *Tetrahedron Letters*, vol. 45, p. 8355-8358, (2004).
Snyder, L.R. et al., *Introduction To Modern Liquid Chromatography*, 2nd Ed., (1979), pp. 549-572, John Wiley & Sons, Inc.
Strobel, H.A. et al., *Chemical Instrumentation: A Systematic Approach*, 3rd Ed., (1989), pp. 391-393, 879-894, 922-925, 953.

*Primary Examiner*—Yvonne Eyler
*Assistant Examiner*—Sudhakar Katakam
(74) *Attorney, Agent, or Firm*—Kenyon & Kenyon LLP

(57) ABSTRACT

Isolated cinacalcet carbamate, processes for the preparation thereof, and processes for the use of cinacalcet carbamate as a reference marker and standard are provided. Also provided are cinacalcet salts substantially free of cinacalcet carbamate, and processes for the preparation thereof.

17 Claims, 1 Drawing Sheet

Typical HPLC chromatogram of Cinacalcet HCl sample clean from the carbamate

| SampleName | MS-1241 | Sample Type | Unknown |
| Vial | 26 | | |
| Injection | 1 | Acq Method Set | CNC Base |
| Injection Volume | 10.00 μl | Processing Method | CNC |
| Channel | 996 | | |
| Run Time | 35.0 Minutes | | |

Processed Channel Descr. PDA 210.0 nm

Peak Results

| | Name | RT | Area | Height | % Area | % Height | Amount |
|---|---|---|---|---|---|---|---|
| 1 | | 8.673 | 3309 | 402 | 0.04 | 0.04 | |
| 2 | | 9.089 | 9227840 | 937366 | 99.85 | 99.88 | |
| 3 | | 11.175 | 3177 | 318 | 0.03 | 0.03 | |
| 4 | | 14.707 | 3331 | 224 | 0.04 | 0.02 | |
| 5 | | 23.568 | 4417 | 206 | 0.05 | 0.02 | |

PURIFICATION OF CINACALCET

CROSS-REFERENCE TO RELATED APPLICATIONS

This application claims the benefit of U.S. provisional application Nos.: 60/684,152, filed May 23, 2005; 60/698,613, filed Jul. 11, 2005; 60/702,918, filed Jul. 26, 2005; 60/734,669, filed Nov. 7, 2005; 60/738,827, filed Nov. 21, 2005; 60/696,981, filed Jul. 5, 2005; 60/697,111, filed Jul. 6, 2005; 60/701,232, filed Jul. 20, 2005; 60/706,910, filed Aug. 9, 2005, 60/735,126, filed Nov. 8, 2005; 60/794,804, filed Apr. 24, 2006; 60/730,050, filed Oct. 24, 2005; 60/732,083, filed Oct. 31, 2005; 60/733,008, filed Nov. 2, 2005; 60/741,787, filed Dec. 1, 2005; and 60/750,910, filed Dec. 15, 2005, hereby incorporated by reference.

FIELD OF THE INVENTION

The present invention relates to the cinacalcet impurity, cinacalcet carbamate.

BACKGROUND OF THE INVENTION (R)-α-methyl-N-[3-[3-(trifluoromethyl)phenyl]propyl]-1-naphthalenemethane amine (herein "Cinacalcet" or "CNC") has a CAS number of 226256-56-0, a formula of $C_{22}H_{22}F_3N$, and the following structure.

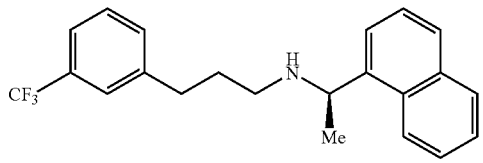

Cinacalet is the free base form of cinacalcet hydrochloride (herein "CNC-HCl"), having a CAS number of 364782-34-3 and the following structure:

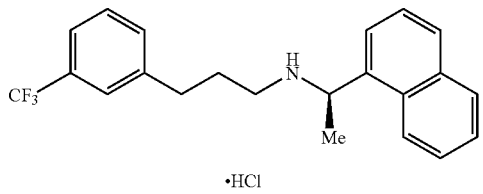

CNC-HCl is marketed as SENSIPAR™, and was the first drug in a class of compounds known as calcimimetics to be approved by the FDA. Calcimimetics are a class of orally active, small molecules that decrease the secretion of parathyroid hormone ("PTH") by activating calcium receptors. The secretion of PTH is normally regulated by the calcium-sensing receptor. Calcimimetic agents increase the sensitivity of this receptor to calcium, which inhibits the release of parathyroid hormone, and lowers parathyroid hormone levels within a few hours. Calcimimetics are used to treat hyperparathyroidism, a condition characterized by the over-secretion of PTH that results when calcium receptors on parathyroid glands fail to respond properly to calcium in the bloodstream. Elevated levels of PTH, an indicator of secondary hyperparathyroidism, are associated with altered metabolism of calcium and phosphorus, bone pain, fractures, and an increased risk for cardiovascular death. As a calcimimetic, CNC-HCl is approved for treatment of secondary hyperparathyroidism in patients with chronic kidney disease on dialysis. Treatment with CNC-HCl lowers serum levels of PTH as well as the calcium/phosphorus ion product, a measure of the amount of calcium and phosphorus in the blood.

Inorganic ion receptor active molecules, especially calcium receptor-active molecules, such as those having the general structure of cinacalcet, are disclosed in U.S. Pat. No. 6,011,068. U.S. Pat. No. 6,211,244 discloses calcium receptor-active compounds related to cinacalcet and methods of making such compounds. Cinacalcet and its enantiomer may be produced by various methods, using the processes disclosed in U.S. Pat. No. 6,211,244; DRUGS OF THE FUTURE, 27 (9), 831 (2002); U.S. Pat. Nos. 5,648,541; 4,966,988; and Tetrahedron Letters (2004) 45: 8355, footnote 12.

Like any synthetic compound, cinacalcet salt can contain process impurities, including unreacted starting materials, chemical derivatives of impurities contained in starting materials, synthetic by-products, and degradation products. It is also known in the art that impurities present in an active pharmaceutical ingredient ("API") may arise from degradation of the API, for example, during storage or during the manufacturing process, including the chemical synthesis.

In addition to stability, which is a factor in the shelf life of the API, the purity of the API produced in the commercial manufacturing process is a necessary condition for commercialization. Impurities introduced during commercial manufacturing processes must be limited to very small amounts, and are preferably substantially absent. For example, the International Conference on Harmonisation of Technical Requirements for Registration of Pharmaceuticals for Human Use ("ICH") Q7A guidance for API manufacturers requires that process impurities be maintained below set limits. The guidance specifies the quality of raw materials, and process parameters, such as temperature, pressure, time, and stoichiometric ratios, including purification steps, such as crystallization, distillation, and liquid-liquid extraction, in the manufacturing process.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as cinacalcet salt, it must be analyzed for purity, typically by high performance liquid chromatography ("HPLC") or thin layer chromatography ("TLC"), to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, are as safe as possible for clinical use. In the United States, the Food and Drug Administration guidelines recommend that the amounts of some impurities be limited to less than 0.1 percent.

Generally, side products, by-products, and adjunct reagents (collectively "impurities") are identified spectroscopically and/or with another physical method, and then associated with a peak position, such as that in a chromatogram or a spot on a TLC plate. See Strobel, H. A.; Heineman, W. R., Chemical Instrumentation: A Systematic Approach, 3rd ed. (Wiley & Sons: New York 1989), p. 953 ("Strobel"). Thereafter, the impurity can be identified, e.g., by its relative position in the chromatogram, where the position in a chromatogram is conventionally measured in minutes between injection of the sample on the column and elution of the particular component through the detector. The relative position in the chromatogram is known as the "retention time."

The retention time can vary about a mean value based upon the condition of the instrumentation, as well as many other factors. To mitigate the effects such variations have upon accurate identification of an impurity, practitioners use the relative retention time ("RRT") to identify impurities. See Strobel p. 922. The RRT of an impurity is its retention time divided by the retention time of a reference marker. It may be advantageous to select a compound other than the API that is added to, or present in, the mixture in an amount sufficiently large to be detectable and sufficiently low as not to saturate the column, and to use that compound as the reference marker for determination of the RRT.

Those skilled in the art of drug manufacturing, research and development understand that a compound in a relatively pure state can be used as a "reference standard." A reference standard is similar to a reference marker, but can be used for quantitative analysis, rather than simply qualitative analysis, as with a reference standard. A reference standard is an "external standard," when a solution of a known concentration of the reference standard and an unknown mixture are analyzed using the same technique. See Strobel p. 924; Snyder, L. R.; Kirkland, J. J. Introduction to Modern Liquid Chromatography, 2d ed. (John Wiley & Sons: New York 1979), p. 549 ("Snyder"). The amount of the compound in the mixture can be determined by comparing the magnitude of the detector response. See U.S. Pat. No. 6,333,198, incorporated herein by reference.

The reference standard can also be used to quantify the amount of another compound in the mixture if a "response factor," which compensates for differences in the sensitivity of the detector to the two compounds, has been predetermined. See Strobel p. 894. For this purpose, the reference standard is added directly to the mixture, and is known as an "internal standard." See Strobel p. 925; Snyder p. 552.

The reference standard can serve as an internal standard when, without the deliberate addition of the reference standard, an unknown mixture contains a detectable amount of the reference standard compound using the technique known as "standard addition."

In the "standard addition technique", at least two samples are prepared by adding known and differing amounts of the internal standard. See Strobel, pp. 391-393; Snyder pp. 571, 572. The proportion of the detector response due to the reference standard present in the mixture without the addition can be determined by plotting the detector response against the amount of the reference standard added to each of the samples, and extrapolating the plot to zero concentration of the reference standard. See, e.g., Strobel, FIG. 11.4, p. 392. The response of a detector in HPLC (e.g. ultraviolet ("UV") detectors or refractive index detectors) can be and typically is different for each compound eluting from the HPLC column. Response factors, as known, account for this difference in the response signal of the detector to different compounds eluting from the column.

As is known by those skilled in the art, the management of process impurities is greatly enhanced by understanding their chemical structures and synthetic pathways, and by identifying the parameters that influence the amount of impurities in the final product.

Impurities in cinacalcet including, but not limited to, unreacted starting materials, by-products of the reaction, products of side reactions, or degradation products are undesirable and, in extreme cases, might even be harmful to a patient being treated with a dosage form containing the API. Thus, there is a need in the art for a method for determining the level of impurities in cinacalcet samples and removing the impurities.

SUMMARY OF THE INVENTION

In one embodiment, the present invention provides a cinacalcet impurity, cinacalcet carbamate, 3-(3-(trifluoromethyl)phenyl)propyl(R)-1(naphthalem-1-yl)ethyl carbamate ("CNC-carbamate"), having the following structure.

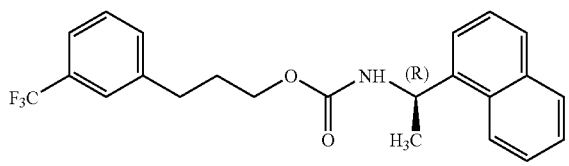

In another embodiment, the present invention provides cinacalcet salt having cinacalcet carbamate in an amount of about 0.03 area percent to about 0.15 area percent as measured by HPLC.

In another embodiment, the present invention provides a method for preparing a cinacalcet salt, cinacalcet hydrochloride, containing cinacalcet carbamate in an amount of about 0.03 area percent to about 0.15 area percent as measured by a chromatographic method, preferably HPLC or TLC, comprising the steps of (a) dissolving cinacalcet base, containing cinacalcet carbamate in an amount of about 3 area percent to about 6 area percent as determined by a chromatographic method, in acetone, a linear or a branch-chain $C_{2-8}$ ether, mixtures thereof or with water; (b) adding hydrogen chloride to obtain a precipitate; and (c) recovering the cinacalcet hydrochloride.

In another embodiment, the present invention provides a process for using cinacalcet carbamate as a reference marker or reference standard. Cinacalcet carbamate can be used as a reference marker for determining the presence of cinacalcet carbamate in a sample of cinacalcet hydrochloride. In addition, cinacalcet carabamate can be used as a reference standard for determining the relative quantity of CNC-carbamate.

In another embodiment, the present invention provides a process for preparing a cinacalcet salt containing CNC-carbamate comprising the steps of (a) obtaining one or more samples of one or more batches of cinacalcet base; (b) measuring the level of CNC carbamate in each of the samples of obtained in step (a); (c) selecting the cinacalcet base batch based on the sample that comprises a level of CNC-carbamate in an amount of about 3 area percent to about 6 area percent as determined by HPLC, based on the measurement or measurements conducted in step (b); and (d) using the batch selected in step (c) to prepare the cinacalcet salt.

When the cinacalcet base sample of step (a) contains more than about 3 area percent by HPLC of CNC-carbamate, according to the measurement in step (b), the sample may be purified prior to performing step (c).

In another embodiment, the present invention provides a pharmaceutical composition comprising cinacalcet base or salts thereof having about 0.03 area percent to about 0.15 area percent as determined by HPLC of cinacalcet carbamate and at least one pharmaceutically acceptable excipient.

In another embodiment, the present invention provides a process for preparing a pharmaceutical composition comprising combining cinacalcet salt having about 0.03 area percent to about 0.15 area percent as determined by HPLC of CNC-carbamate with at least one pharmaceutically acceptable excipient.

DETAILED DESCRIPTION OF THE INVENTION

Figure 1:
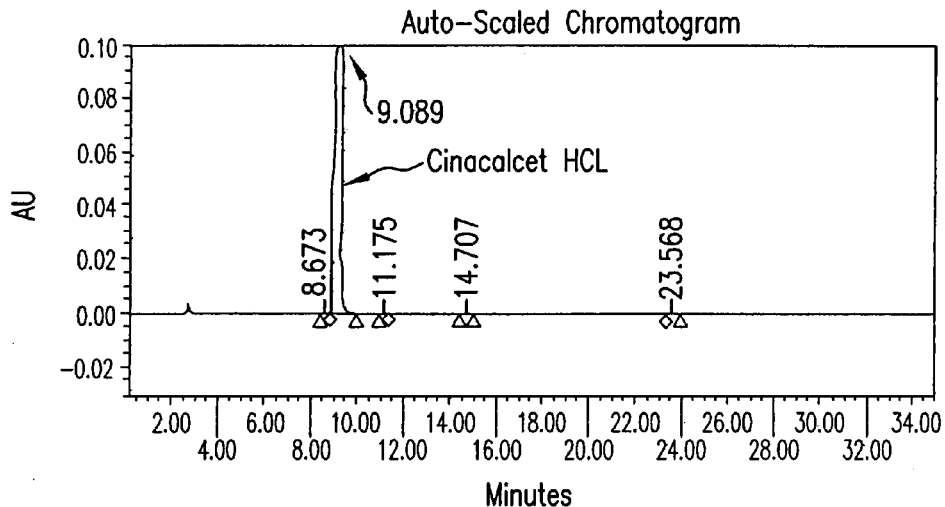
FIG. 1 illustrates a typical HPLC chromatogram of Cinacalcet HCl sample substantially free of the carbamate.

As used herein, room temperature is meant to indicate a temperature of about 18 to about 25° C., preferably about 20 to about 22° C.

As used herein, "CNC" refers to cinacalcet.

As used herein, "cinacalcet salt" may be any salt that has a pKa lower than the pKa of cinacalcet base. Appropriate acids that can be used to form such salts may include HCl, HBr, $H_2SO_4$, oxalic acid, tartaric acid, succinic acid and citric acid. More preferably, the cinacalcet salt is cinacalcet HCl As used herein, the term "reference marker" is used in qualitative analysis to identify components of a mixture based upon their position, e.g., in a chromatogram or on a Thin Layer Chromatography (TLC) plate. See Strobel pp. 921, 922, 953. For this purpose, the compound does not necessarily have to be added to the mixture if it is present in the mixture. A "reference marker" is used only for qualitative analysis, while a reference standard may be used for quantitative or qualitative analysis, or both. Hence, a reference marker is a subset of a reference standard, and is included within the definition of a reference standard.

As used herein, the term "reference standard" refers to a compound that may be used both for quantitative and qualitative analysis of an active pharmaceutical ingredient. For example, the HPLC retention time of the compound allows a relative retention time to be determined, thus making qualitative analysis possible. The concentration of the compound in solution before injection into an HPLC column allows the areas under the HPLC peaks to be compared, thus making quantitative analysis possible.

Reference standards are described in general terms above. However, as will be understood by those skilled in the art, a detector response can be, for example, the peak heights or integrated peak areas of a chromatogram obtained, e.g., by UV or refractive index detection, from the eluent of an HPLC system or, e.g., flame ionization detection ("FID") or thermal conductivity detection, from the eluent of a gas chromatograph, or other detector response, e.g., the UV absorbance of spots on a fluorescent TLC plate. The position of the reference standard may be used to calculate the relative retention time for cinacalcet salts and impurities of cinacalcet salts.

In one embodiment, the present invention provides a cinacalcet impurity, cinacalcet carbamate ("CNC-carbamate"), having a molecular weight of 401 g/mole as measured by mass spectroscopy ("MS") analysis, and having the formula.

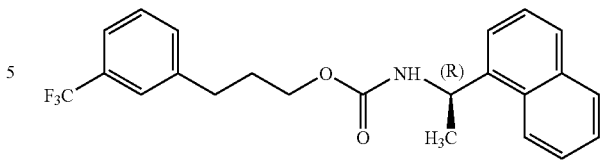

The CNC-carbamate of the present invention may be characterized by data selected from a $^1$H NMR spectrum having hydrogen chemical shifts at about 1.67, 1.95, 2.73, 4.12, 5.11, 5.68, and 7.35-8.15 ppm; a $^{13}$CNMR spectrum having carbon chemical shifts at about 21.59, 30.42, 31.96, 46.58, 63.99, 122.16-142.23, and 155.63 ppm; and by a retention time ("RT") of about 22-23 minutes in HPLC analysis or relative retention time ("RRT") of about 2.6, such as the one described herein below.

CNC-carbamate may form in the synthesis of cinacalcet base for example, by the processes disclosed in U.S. Provisional Applications Nos. 60/681,671 and 60/702,918. This process comprises combining mesylate (FTOMs) of formula II:

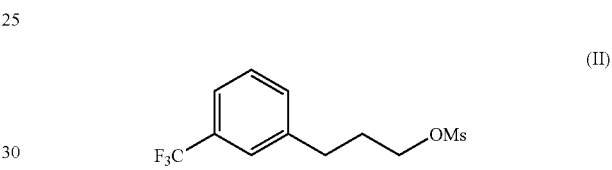

(II)

with (R)-Naphtylethyl amine ("R-NEA") of formula III:

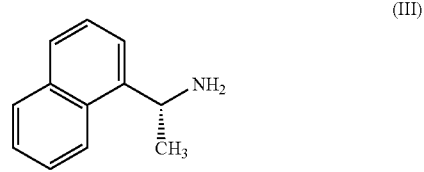

(III)

in the presence of a base with a solvent at elevated temperature, to give CNC base of formula (IV):

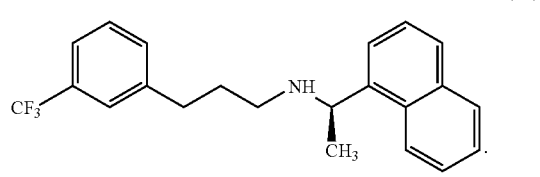

(IV)

The CNC base can be further reacted with an acid to form cinacalcet salt. The selected cinacalcet salt may be any salt that has a pKa lower than the pKa of cinacalcet base. Appropriate acids that can be used to form such salts may be HCl, HBr, $H_2SO_4$, oxalic acid, tartaric acid, succinic acid and citric acid. More preferably, the cinacalcet salt is cinacalcet HCl.

CNC-carbamate may be formed in various amounts while using different solvents during the synthesis of the cinacalcet base as shown in Table 1.

TABLE 1

| Solvent | % Conversion of Compound (II) to CNC base | Temperature | Time | Level of CNC-carbamate (% area by HPLC) |
|---|---|---|---|---|
| Acetone | 60% | reflux (56° C.) | 88 hrs | 1.6 |
| Methyl iso-butyl ketone ("MIBK") | 81% | reflux (120° C.) | 13 hrs | 11.5 |
| MIBK | 78% | reflux (80° C.) | 13 hrs | 4.4 |
| Isopropanol ("IPA") | 88% | reflux (80° C.) | 17 hrs | 7.2 |
| Ethyl acetate ("EtOAc") | 80% | reflux (76° C.) | 30 hrs | 7.0 |
| Ethanol ("EtOH") | 68% | reflux (78° C.) | 3 hrs | 10.0 |
| Acetonitrile ("ACN") | 93% | reflux (81° C.) | 16 hrs | 2.9 |
| Toluene without PTC | 81% | reflux (110° C.) | 14 hrs | 12.0 |
| Toluene with PTC (TBAB) | 39% | 80° C. | 13 hrs | 40.5 |
| Toluene with PTC (aliquat 336) | 23% | 80° C. | 2.5 hrs | 31.0 |

In another embodiment of the present invention, isolated CNC-carbamate is provided. CNC-carbamate formed during the synthesis of cinacalcet base may be isolated by subjecting the cinacalcet base that contains the CNC-carbamate to column chromatography. The column chromatography comprises using a silica gel, as a stationary phase, and a gradient of eluents that remove CNC-carbamate from the column on which it adsorbed, starting from 100 percent n-hexane to 20 percent ethyl acetate/80 percent n-hexane over a period of 10 minutes.

In the column chromatography described above, the stationary phase, a solid adsorbent, is placed in a vertical glass (usually) column and the mobile phase, a liquid is added to the top and flows down through the column (by either gravity or external pressure). Column chromatography is generally used as a purification technique; it isolates desired compounds from a mixture. The mixture to be analyzed by column chromatography is applied to the top of the column. The liquid solvent (the eluent) is passed through the column by gravity or by the application of air pressure. Equilibrium is established between the solute adsorbed on the adsorbent and the mobile phase flowing down through the column. Because the different components in the mixture have different interactions with the stationary and mobile phases, they will be carried along with the mobile phase to varying degrees and a separation will be achieved. The individual components, or eluents, are collected as the solvent drips from the bottom of the column.

In another embodiment, the present invention provides cinacalcet salt having CNC-carbamate in an amount of about 0.03 area percent to about 0.15 area percent as determined by a chromatographic method. Preferably, the cinacalcet salt is cinacalcet HCl.

In yet another embodiment, the present invention provides a method for preparing cinacalcet HCl containing CNC-carbamate in an amount of about 0.03 to about 0.15 area percent as measured by a chromatographic method, preferably HPLC or TLC comprising the steps of (a) dissolving cinacalcet base, containing cinacalcet carbamate in an amount of about 3 area percent to about 6 area percent as determined by a chromatographic method, in acetone, a linear or a branch-chain $C_{2-8}$ ether, mixtures thereof or with water; (b) admixing hydrogen chloride to obtain a precipitate; and (c) recovering the cinacalcet hydrochloride.

The preferred solvent is acetone or methyl tert-butyl ether ("MTBE"). The HCl added may be in the form of a gas or in an aqueous solution. Preferably, the HCl is added as a gas. More preferably, the gaseous HCl is added in an amount of about 1 to 2 equivalents relative to cinacalcet base. When the HCl is aqueous, it is preferably added at a concentration of about 1N in an amount of about 1.5 equivalents. Preferably, the reaction is at room temperature. The obtained cinacalcet HCl may be in crystalline form.

In another aspect of the present invention, provided is the use of CNC-carbamate as a reference marker or reference standard.

The use of cinacalcet carbamate as a reference marker for determining the presence of cinacalcet carbamate in cinacalcet base or salt is by the process comprising (a) determining the retention time by a column chromatographic method, such as HPLC or TLC, corresponding to the cinacalcet carbamate in a reference marker comprising CNC carbamate; (b) running a sample of cinacalcet base or salt on a column chromatography method; and (c) using the retention time in step (a) to identify the presence of cinacalcet carbamate in the sample.

In another embodiment, a method is provided for determining the amount of CNC carbamate in cinacalcet salt or a base comprising (a) using a chromatographic method such as HPLC or TLC to measure the area under a peak corresponding to CNC carbamate in a reference standard comprising a known amount of CNC carbamate; and (b) determining the level of CNC carbamate in the sample by comparing the area of step (a) to the area under the peak in a sample comprising a cinacalcet salt or base contaminated with CNC carbamate.

The skilled artisan will have no difficulty performing the chromatographic method. In one example, an HPLC method includes the steps of (a) combining a sample of CNC with a mixture of acetonitrile and water at a ratio of 1:1 to obtain a solution; (b) injecting the solution into a 100×4.6 mm BDS Hypersil C-18 (or similar) column, which is maintained at room temperature; (c) gradually eluting the sample from the column using a mixture of buffer:acetonitrile at a ratio of 3:2 by volume, and acetonitrile and a mixture of buffer:acetonitrile:ethanol at a ratio of 2:9:9 as an eluent; and (d) measuring the amount of CNC carbamate in the relevant sample with a UV detector, preferably at a 243 nm wavelength.

In yet another aspect of the present invention, provided is a process for preparing a cinacalcet salt comprising CNC carbamate in an amount of about 0.03 area percent to about 0.15 area percent as determined by a chromatographic method comprising the steps of (a) providing one or more samples of one or more batches of cinacalcet base; (b) measuring the level of CNC carbamate in each of the samples of (a); (c) selecting the cinacalcet base batch based on the sample that comprises a level of CNC carbamate in an amount of about 3 area percent to about 6 area percent as determined by HPLC, based on the measurement or measurements conducted in step (b); and (d) using the batch selected in step (c) to prepare said Cinacalcet salt.

Preferably, the prepared cinacalcet salt of step (d) is in an amount of about 0.03 area percent to about 0.15 area percent as determined by HPLC.

When the cinacalcet base sample of step (a) contains more than about 3 area percent of CNC carbamate, according to the measurement in step (b), the sample may be purified, prior to performing step (c).

In yet another aspect, the present invention provides a pharmaceutical composition comprising cinacalcet base or salts having about 0.03 percent to about 0.15 percent area by HPLC of cinacalcet carbamate, optionally prepared by any of the methods mentioned above; and at least one pharmaceutically acceptable excipient.

In one aspect, the present invention provides a process for preparing a pharmaceutical composition comprising combining cinacalcet salt having about 0.03 percent to about 0.15 percent area by HPLC of CNC-carbamate with at least one pharmaceutically acceptable excipient.

EXAMPLES

| HPLC method | HPLC method for analyzing the CNC-carbamate |
|---|---|
| Column & packing | Hypersil GOLD 250 mm 4.6 mm 3μ C.N 25003-254630 |
| Eluent | 40% - 0.02 M $KH_2PO_4$ adjusted to pH = 6.0 with KOH<br>60% - Acetonitrile |
| Stop time: | 35 min |
| Flow: | 1.0 ml/min |
| Detector: | 210 nm. |
| Injection volume: | 10 μl. |
| Diluent | 50% Water:50% ACN |
| Column temperature | Ambient |

Samples of cinacalcet HCl are prepared by weighing accurately about 10 mg of cinacalcet HCl into a 50 ml volumetric flask, dissolving and diluting to volume with diluent. Samples are then injected into the HPLC column, continuing the chromatogram up to the end of the gradient. The area of each impurity is determined using a suitable integrator.

Any impurity in a sample is calculated as follows:

$$\% \text{ Impurity in sample} = \frac{\text{area impurity in sample}}{\sum \text{Areas of all peaks}} \times 100$$

A sample of CNC was combined with a mixture of acetonitrile and water at a ratio of 1:1 to obtain a solution. The solution was injected into a 100×4.6 mm BDS Hypersil C-18 (or similar) column, at room temperature. The sample was gradually eluted from the column using a mixture of buffer:acetonitrile at a ratio of 3:2 by volume, and acetonitrile and a mixture of buffer:acetonitrile:ethanol at a ratio of 2:9:9 as an eluent; and measuring the amount of CNC carbamate, in the relevant sample with a UV detector, preferably at a 243 nm wavelength.

Preparation of Cinacalcet Base Substantially Contaminated with CNC Carbamate

Example 1

25.5 g of mesylate (FTOMs) were dissolved in acetonitrile (204 ml). (R)-1-naphtylethyl amine (14.5 ml) and anhydrous $K_2CO_3$ (24.9 g) were added and the reaction mixture was heated to reflux temperature and maintained at reflux for 16 hours. Then salts were filtered out and the solvent was removed under reduced pressure. The residue was dissolved in DCM (75 ml). The obtained solution was washed with 5 percent aqueous HCl solution (pH=1), followed by a saturated solution of $NaHCO_3$ (pH=8-9), and finally with water. The organic phase was separated and dried over $Na_2SO_4$ and filtered. The solvent was evaporated until dryness to obtain 33.4 g of cinacalcet base that contained 3 area percent by HPLC of CNC-carbamate.

Example 2

10.0 g of mesylate (FTOMs) (1 eq.) were dissolved in toluene (60 ml). (R)-1-naphtylethyl amine (0.98 eq.) and anhydrous $K_2CO_3$ (2 eq.) were added and the reaction mixture was heated to reflux temperature and maintained at reflux for 14 hours. Then salts were filtered out and the solvent was removed under reduced pressure. The residue was dissolved in DCM (75 ml). The obtained solution was washed with 5 percent aqueous HCl solution (pH=1), followed by a saturated solution of $NaHCO_3$ (pH=8-9), and finally with water. The organic phase was separated and dried over $Na_2SO_4$ and filtered. The solvent was evaporated until dryness to obtain 11.0 g of Cinacalcet base that contained 12 area percent by HPLC of CNC-carbamate.

Example 3

5.0 g of mesylate (FTOMs) (1 eq.) were dissolved in Toluene (80 ml). (R)-1-naphtylethyl amine (0.98 eq.) and anhydrous $K_2CO_3$ (2 eq.) were added and the reaction mixture was heated to 80° C. for 12 hours. Then tetrabutyl ammonium bromide ("TBAB") (5 percent per mole of FTOMs) was added. The mixture was heated for an additional hour at 80° C. Salts were filtered out and the solvent was removed under reduced pressure. The residue was dissolved in DCM (75 ml). The obtained solution was washed with 5 percent aqueous HCl solution (pH=1), followed by a saturated solution of $NaHCO_3$ (pH=8-9), and finally with water. The organic phase was separated and dried over $Na_2SO_4$ and filtered. The solvent was evaporated until dryness to obtain cinacalcet base that contained 40.5 area percent by HPLC of CNC-carbamate. CNC-carbamate was isolated by column chromatography on Silica gel; gradient of eluent: 100 percent n-hexane—20 percent ethyl acetate/80 percent n-hexane during 10 minutes.

Purification Process—Preparation of Cinacalcet Hydrochloride Substantially Pure of CNC Carbamate from Contaminated Cinacalcet Base Example 4

Cinacalcet base (2.0 g) prepared according to Example 1 was dissolved in acetone (4 ml) at room temperature. Then 1N HCl (1.5 eq.) and water (40 ml) were added. The mixture was stirred at room temperature for 4 hours to obtain a precipitate. The product was isolated by filtration, washed with water (10 ml) and dried at 50° C. in a vacuum oven for 24 hours to obtain 1.75 g of cinacalcet hydrochloride containing less than 0.15 area percent of CNC-carbamate as measured by HPLC. (purity by HPLC 99.9 percent).

Example 5

CNC base (3.15 g) was dissolved in MTBE (15 vol.) at room temperature. HCl gas was bubbled into the obtained solution until no further crystallization of cinacalcet hydrochloride was observed. The slurry was stirred at room temperature for an additional 1 hour. The product was then isolated by filtration, washed with MTBE (2×2 ml) and dried in a vacuum oven at 50° C. for 16 hours to obtain 1.93 g of CNC HCl containing less than 0.1 area percent of CNC-carbamate by HPLC.

Example 6

CNC base (3.0 g) was dissolved in MTBE (20 vol.) at room temperature. HCl gas was bubbled into the obtained solution until no further crystallization of cinacalcet hydrochloride was observed. The slurry was stirred at room temperature for an additional 1 hour. The product was then isolated by filtration, washed with MTBE (2×2 ml) and dried in a vacuum oven at 50° C. for 15 hours to obtain 2.08 g of CNC HCl containing less than 0.1 area percent of CNC carbamate by HPLC.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

What is claimed is:

1. A Cinacalcet impurity, Cinacalcet carbamate, having the formula:

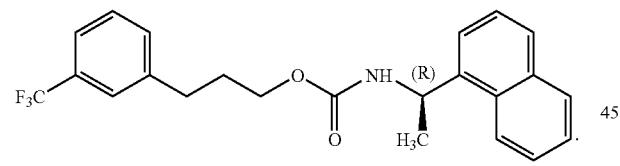

2. An isolated Cinacalcet carbamate impurity of claim 1.

3. A Cinacalcet salt, comprising the Cinacalcet impurity of claim 1 in an amount of about 0.03 area percent to about 0.15 area percent.

4. The Cinacalcet salt of claim 3, wherein the salt is Cinacalcet hydrochloride.

5. A method for preparing the Cinacalcet hydrochloride of claim 4, comprising the steps of:
  a. dissolving Cinacalcet base, containing Cinacalcet carbamate in an amount of about 3 percent to about 6 percent, in a solvent selected from the group consisting of acetone, a linear or a branched-chain $C_{2-8}$ ether, mixtures thereof, and water;
  b. admixing hydrogen chloride to obtain a precipitate; and
  c. recovering the Cinacalcet hydrochloride.

6. The method of claim 5, wherein the solvent is acetone or methyl tert-butyl ether.

7. The method of claim 5, wherein the hydrogen chloride is gaseous or an aqueous solution.

8. The method of claim 7, wherein the hydrogen chloride is gaseous.

9. A process for using Cinacalcet carbamate as a reference marker for determining the presence of Cinacalcet carbamate in Cinacalcet base or salt comprising:
  a) determining a retention time, corresponding to Cinacalcet carbamate, by a chromatographic method in a reference marker, comprising the Cinacalcet carbamate of claim 1;
  b) running a sample of Cinacalcet base or salt with the chromatography method; and
  c) using the retention time in step (a) to identify the presence of Cinacalcet carbamate in the sample.

10. The process of claim 9, wherein the chromatographic method is HPLC or TLC.

11. A process for using Cinacalcet carbamate as a reference standard for determining the amount of Cinacalcet carbamate in a Cinacalcet salt or base, comprising using a chromatographic method to measure the area under a peak corresponding to Cinacalcet carbamate in a reference standard, the reference standard comprising a known amount of the Cinacalcet carbamate of claim 1; and determining the level of Cinacalcet carbamate in the sample by comparing the measured area of the peak to the area under a peak measured in a sample comprising a Cinacalcet salt or base contaminated with Cinacalcet carbamate.

12. The process of claim 11, wherein the chromatographic method is HPLC or TLC.

13. A process for preparing a Cinacalcet salt, comprising Cinacalcet carbamate of claim 1 in an amount of about 0.03 to about 0.15 area percent, as determined by HPLC, the process comprising the steps of:
  (a) providing one or more samples of one or more batches of Cinacalcet base;
  (b) measuring the level of Cinacalcet carbamate in each of the samples of (a);
  (c) selecting the Cinacalcet base batch based on the sample that comprises a level of Cinacalcet carbamate in an amount of about 3 area percent to about 6 area percent as determined by HPLC, based on the measurement or measurements conducted in step (b);
  (d) using the batch selected in step (c) to prepare the Cinacalcet salt;
  (e) dissolving the batch in a solvent selected from the group consisting of acetone, a linear or a branched-chain $C_{2-8}$ ether, mixtures thereof, and water;
  (f) admixing an acid to obtain a precipitate; and
  (g) recovering the Cinacalcet salt.

14. The process of claim 13, wherein the Cinacalcet salt of step (d) is in an amount of about 0.03 to about 0.15 area percent as determined by HPLC.

15. A process for preparing a Cinacalcet salt, comprising the Cinacalcet carbamate of claim 1 in an amount of about 0.03 to about 0.15 area percent, as determined by HPLC, the process comprising the steps of:
  (a) providing one or more samples of one or more batches of Cinacalcet base;
  (b) measuring the level of Cinacalcet carbamate in each of the samples of (a);
  (c) selecting the Cinacalcet base batch based on the sample that comprises a level of Cinacalcet carbamate in an amount greater than 0.15 area percent as determined by HPLC, based on the measurement or measurements conducted in step (b);

(d) using the batch selected in step (c) to prepare the Cinacalcet salt;
(e) dissolving the batch in a solvent selected from the group consisting of acetone, a linear or a branched-chain $C_{2-8}$ ether, mixtures thereof, and water;
(f) admixing an acid to obtain a precipitate; and
(g) recovering the Cinacalcet salt.

16. A pharmaceutical composition, comprising a Cinacalcet salt having about 0.03 percent to about 0.15 percent area by HPLC of the Cinacalcet carbamate of claim 1 and at least one pharmaceutically acceptable excipient.

17. A process for preparing a pharmaceutical composition comprising, combining a Cinacalcet salt, containing about 0.03 percent to about 0.15 percent area by HPLC of the Cinacalcet carbamate of claim 1, with at least one pharmaceutically acceptable excipient.

* * * * *